United States Patent
Charles

(10) Patent No.: US 7,066,918 B2
(45) Date of Patent: Jun. 27, 2006

(54) CLOSED COUPLED URINE COLLECTION CHAMBER

(76) Inventor: Herbert N. Charles, 7685 Riverview Line, Chatham ON (CA), N7M 5J5

( * ) Notice: Subject to any disclaimer, the term of this patent is extended or adjusted under 35 U.S.C. 154(b) by 679 days.

(21) Appl. No.: 10/198,532

(22) Filed: Jul. 18, 2002

(65) Prior Publication Data

US 2003/0073977 A1 Apr. 17, 2003

Related U.S. Application Data

(60) Provisional application No. 60/329,097, filed on Oct. 15, 2001.

(51) Int. Cl.
*A61M 1/06* (2006.01)
*A61F 5/44* (2006.01)

(52) U.S. Cl. .................... 604/327; 604/349
(58) Field of Classification Search ......... 604/327–331, 604/544, 349–353
See application file for complete search history.

(56) References Cited

U.S. PATENT DOCUMENTS

| | | |
|---|---|---|
| 1,372,101 A | 3/1921 | Snow |
| 2,573,449 A | 10/1951 | Johnson |
| 5,618,277 A * | 4/1997 | Goulter .................... 604/349 |
| 5,735,837 A * | 4/1998 | Ishikawa ............... 604/385.09 |
| 5,792,127 A | 8/1998 | Marran |
| 6,045,542 A | 4/2000 | Cawood |
| 6,129,714 A | 10/2000 | Kocsi |
| 6,132,408 A * | 10/2000 | Lutz ........................ 604/335 |
| 6,152,903 A * | 11/2000 | Falconer .................... 604/351 |

FOREIGN PATENT DOCUMENTS

| | | |
|---|---|---|
| GB | 2094632 | 9/1982 |
| GB | 2239804 | 7/1991 |

* cited by examiner

*Primary Examiner*—John J. Calvert
*Assistant Examiner*—Linh Truong
(74) *Attorney, Agent, or Firm*—Carlson, Gaskey & Olds

(57) ABSTRACT

A liquid waste collection chamber assembly adapted to be worn in the crotch region of a user includes a triangular collection chamber with a rigid inlet tube and a back flow valve. The inlet tube attaches to a condom catheter by way of a flexible tube. Liquid waste from the user flows into the collection chamber in response to gravitational force. The collection chamber is worn, attached and supported to the wearer in the crotch region by way of straps connected to a top portion of the collection chamber. The collection chamber also includes an outlet tube disposed above the inlet tube at a top portion of the collection chamber attached. The outlet valve is actuatable to open and allow expulsion of liquid waste from the collection chamber.

23 Claims, 3 Drawing Sheets

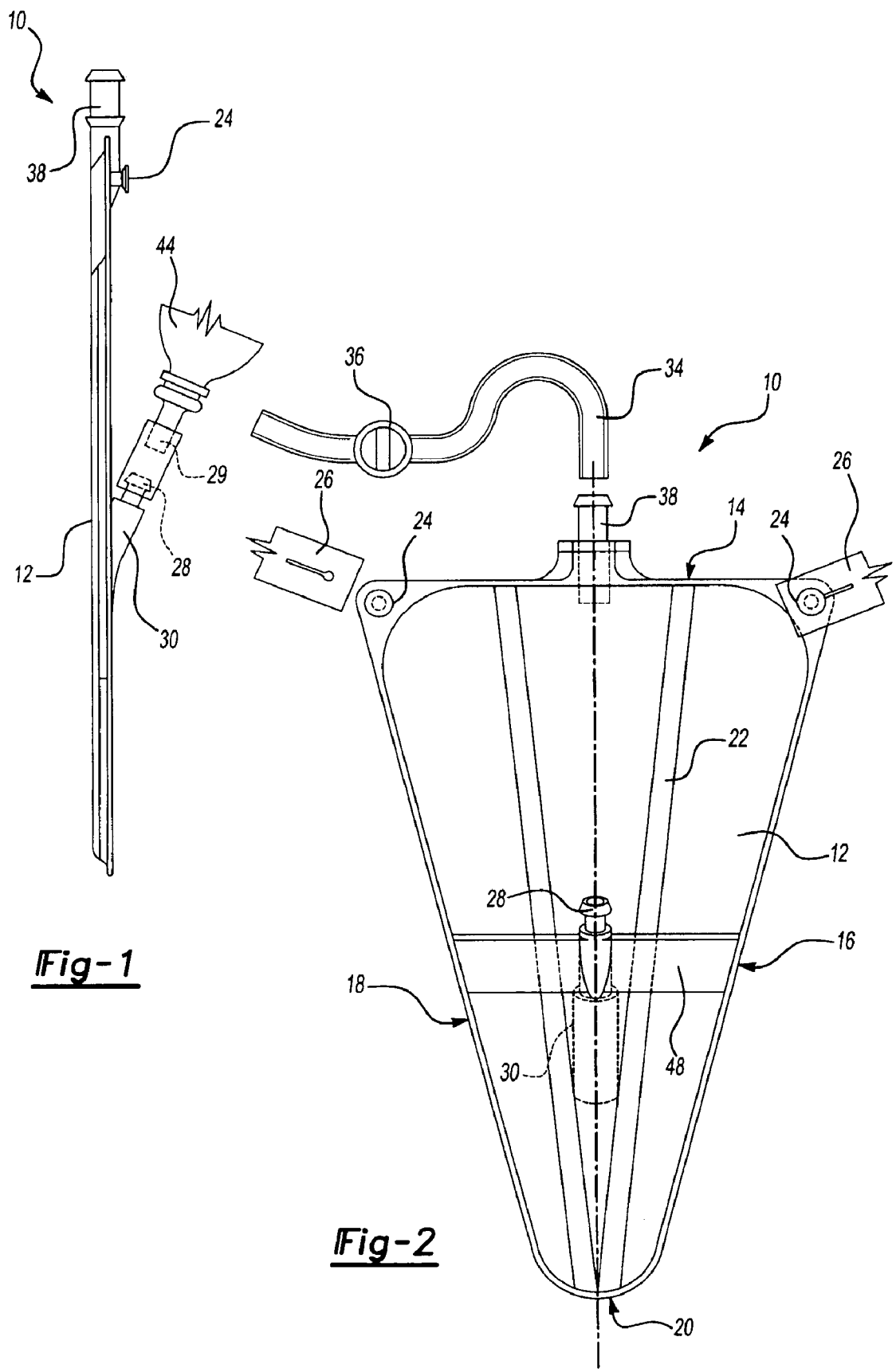

CLOSED COUPLED URINE COLLECTION CHAMBER

RELATED APPLICATIONS

This application claims priority to U.S. Provisional Application Ser. No. 60/329,097; filed on Oct. 15, 2001.

BACKGROUND OF THE INVENTION

This invention relates generally to an assembly for collecting and disposing of fluid waste that cannot be retained by the body and specifically to a collection chamber for accumulating liquid waste for later disposal.

Incontinent males require a device for absorbing and collecting liquid waste that cannot be held within the body due to medical or physical conditions. Conventional methods of absorbing and accumulating this liquid waste include the use of absorbent devices worn to capture liquid waste that cannot be held within the body by normal physical means. Such absorbent devices include undergarments, much like diapers, that are worn under outer garments and of which are disposed after becoming saturated with liquid waste. Such garments are bulky and uncomfortable for the wearer and substantially limit the activities the wearer can undertake while wearing the undergarment. Further, even the most well designed absorbent undergarments inhibit actions and prevent the wearer from participating in activities that they would otherwise undertake.

Another type of device to aid incontinent males is a collection chamber device. Collection chamber devices include an expandable collection chamber that accumulates liquid waste for disposal at a later time. A catheter is worn by the wearer and liquid waste is fed into the collection chamber. The collection chamber must be positioned to allow gravity to draw the liquid waste into the collection chamber. For this reason, the specific location of the collection chamber is limited to regions below the pelvis and below the catheter worn by the wearer. Many such devices are currently known and include a collection pouch that is strapped to a leg of the wearer to provide for sufficient gravitational forces to evacuate the liquid waste into the collection chamber. As appreciated, the wearing of a collection chamber around ones leg is limiting and uncomfortable. Further, wearing a collection chamber on a leg would limit a number of activities and prevent the wearer from wearing shorts or many other types of garments which would be worn absent the incontinent condition.

There is also known a device that includes a collection chamber worn around the abdomen region of the wearer that depends on pressure generated by the wearer in evacuating liquid waste to draw the liquid waste from the crotch region upward to the collection chamber secured about the abdomen of the wearer. This device still does not provide the comfort and mobility desired by persons with this affliction. Further, because this device depends on pressures created by the wearer it may not be feasible for all persons with incontinent conditions. In other words, there maybe certain incontinent conditions where the wearer is unable to produce enough internal pressure to drive liquid waste upward from the crotch region into a collection chamber secured about the abdomen of the wearer.

Accordingly, there is a need for a device to accumulate liquid waste that is comfortable and wearable to allow incontinent males to participate in activities while comfortably and dependably accumulating liquid waste for later disposal.

SUMMARY OF THE INVENTION

An embodiment of this invention is a collection chamber wearable in the crotch region of the wearer and that is emptyable in a discreet manner such that the wearer is not required to remove garments to expel liquid waste accumulated in the collection chamber.

An embodiment of this invention is a collection chamber wearable in the crotch region of an incontinent male and includes a rigid tube affixed within a collection chamber including a back flow prevention valve. The collection chamber is generally triangularly shaped for comfortable wearing within the crotch region of the wearer. The collection chamber is preferably fabricated from a plastic, pleated material that expands upon the accumulation of liquid waste. The collection chamber shape facilitates the comfortable wearing in the crotch region much like an athletic cup or athletic supporter.

Liquid waste flows into the collection chamber to the wearer through a flexible tube attached to a condom catheter. The condom catheter is disposed in a position above the rigid tube of the collection chamber to allow gravitational forces to drive liquid waste expelled by the wearer into the collection chamber. The collection chamber includes a back flow valve that is preferably a duct filled type back flow valve. The back flow valve prevents any liquid waste from refluxing or returning through the inlet tube and back towards the wearer. The collection chamber also includes an outlet tube. The outlet tube is a rigid tube fixed to an upper portion of the collection chamber above the inlet tube. The outlet tube attaches to a flexible tube that includes an outlet valve. The outlet valve is actuatable between an open and closed position and allows for the discrete evacuation of the liquid waste within the collection chamber.

In practice, the collection chamber will be emptied by a wearer by extending the outlet tube, opening the outlet valve and exerting pressure on the collection chamber to expel liquid waste through the outlet. The collection chamber is secured in the crotch region of the wearer by a strap in much the same manner that an athletic supporter or cup is worn. This provides for increased comfort for the wearer and allows the wearer to wear any type of clothing. Further, the discrete location of the collection chamber allows participation in many activities that may not have otherwise been possible for the wearer.

Accordingly, the collection chamber of this device provides for a comfortable and substantially non-interfering collection chamber for a wearer that can be discreetly worn and emptied allowing participation in activities that may have otherwise been uncomfortable or unreasonable.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows:

FIG. 1 is a side view of the collection chamber assembly;

FIG. 2 is a plan view of the collection chamber;

DETAILED DESCRIPTION OF THE PREFERRED EMBODIMENT

Figure 3:
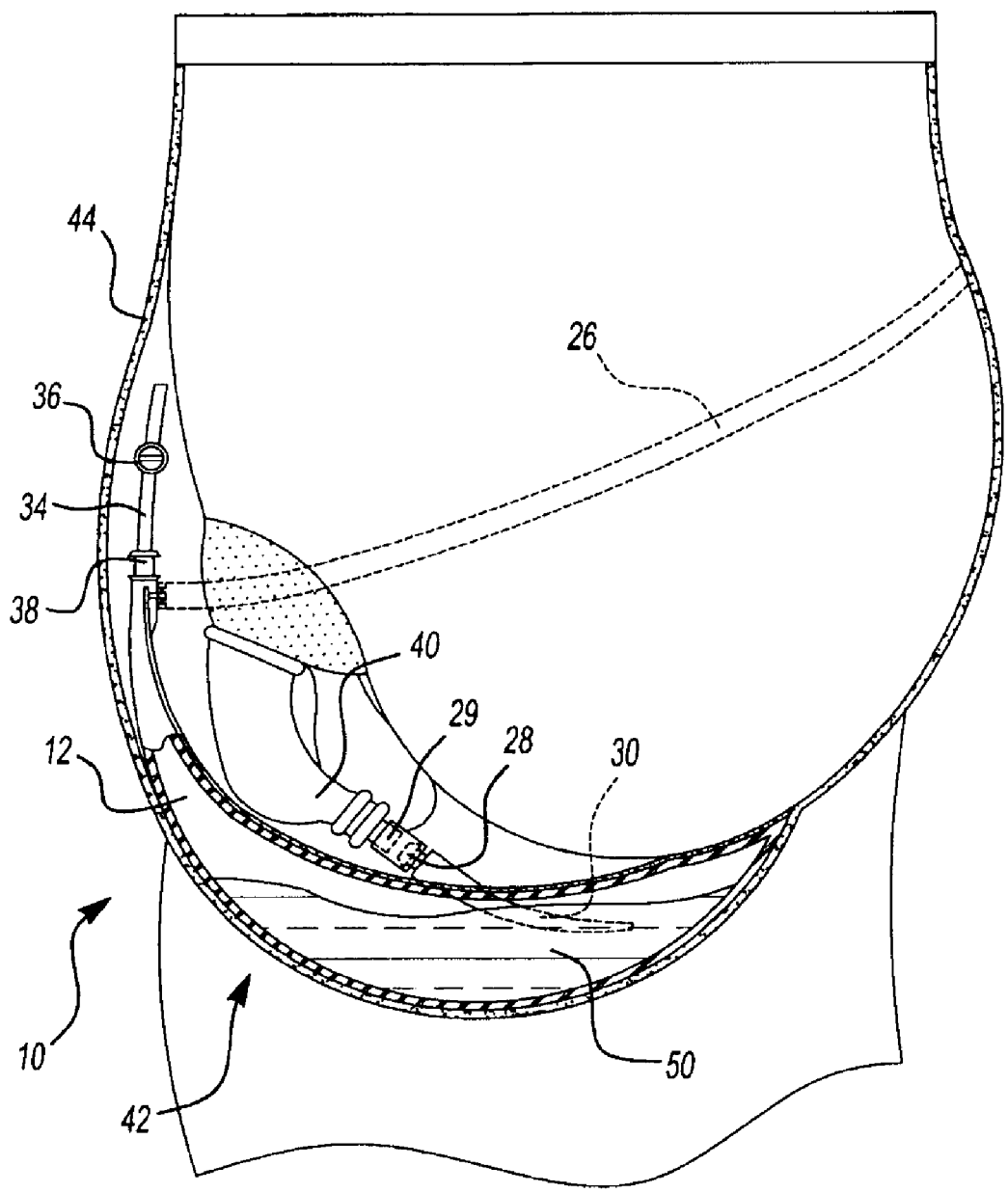
FIG. 3 is a side view of the collection chamber as worn by a wearer.

Referring to the FIGS. 1 and 2, a collection assembly 10 includes a collection chamber 12 with a ridge tube 28 forming an inlet. The collection chamber 12 includes topside 14 and first and second sides 16, 18. The collection chamber 12 is configured in a generally triangular shape including the topside 14, and first and second sides 16, 18 that converge at a common point 20. The triangular shape facilitates wearing in the crotch region of the wearer providing increased comfort and activity. The collection chamber is preferably constructed of a plastic or rubber material, however other materials as known to a worker skilled in the art are within the contemplation of this invention.

Preferably, the collection chamber 12 includes pleats 22 that allow expansion as liquid waste or urine is collected. Preferably, the collection chamber 12 is sized such that between 150–250 milliliters of waste liquid can be comfortably collected. The amount of liquid storage within the collection chamber 12 preferably provides between three and four hours of collection of liquid waste for the wearer. As appreciated, the specific size of the collection chamber 12 is application specific and it is within the contemplation of this invention that the collection chamber 12 may be a differing size.

The inlet tube 28 is rigidly constructed and fixed to the collection chamber 12. The rigid tube 28 is sealed to the collection chamber and is an integral part of the collection chamber 12. Attached to the rigid tube 28 and extending into the collection chamber 12 is a back flow valve 30. The back flow valve 30 prevents liquid waste within the collection chamber 12 from refluxing or moving upward out of the collection chamber 12 through the inlet tube 28. Preferably, the back flow valve 30 is of a duck billed type. As appreciated, a duck billed type back flow valve is common to devices within this art and a worker skilled within the art would understand that other types of back flow valves are also within the contemplation of this invention.

Attached to the inlet tube 28 is a flexible tube 29. The flexible tube 29 is in turn attached to a condom type catheter 44. This provides full communication between the condom catheter 44 and the collection chamber 12. Liquid waste proceeds in response to gravitational forces through the condom catheter 44, the tube 29 and the inlet tube 28 into the collection chamber 12. Once liquid waste is within the collection chamber 12, the back flow valve 30 prevents liquid waste from returning through and out the inlet tube 28. The inlet tube 28 is affixed to the collection chamber 12 and is affixed in a region including a strengthening strip 48.

The top side 14 of the collection chamber 12 includes buttons 24. The buttons 24 correspond to straps 26 that secure the collection chamber 12 in the crotch region of the wearer. At the topside 14 of the collection chamber 12 is an outlet tube 38 connected to flexible tube 34 including an outlet valve 36. The outlet valve 36 is closed until evacuation of the collection chamber 12 is desired.

Referring to FIG. 3, the assembly 10 is shown as is worn by an incontinent male. The collection chamber 12 is secured to the wearer by way of the straps 26. The straps 26 secure the topside 14 of the collection chamber 12 to the wearer and the lower point 20 is disposed within the crotch region (generally indicated at 42) toward the rear of the wearer. The undergarment that the wearer assists in supporting the collection chamber 12 within the crotch region 42. Outer garment 44 fits over the collection chamber assembly 10 in a non-obvious manner and provides for the discrete collection of liquid waste from the wearer. As is indicated by arrow 50, liquid waste accumulates within the collection chamber 12 and in the crotch region 42 of the wearer. Liquid waste 50 within the collection chamber 12 is prevented from back flowing through the inlet tube 28 by the back flow valve 30.

The condom catheter 40 provides for the fluid communication of liquid waste from the wearer through flexible tube 29 and inlet tube 28 and back flow valve 30. The topside 14 of the collection chamber 12 is disposed above the condom catheter 40. Further, the inlet tube 28 is disposed at a point below the condom catheter 40 such that gravitational forces draw liquid waste from the wearer into the collection chamber 12. The outlet tube 38 is disposed at a point above the condom catheter 40 and is discreetly stored under the outer garment 44.

Positioning the collection chamber 12 within the crotch region 42 of the wearer allows for the discrete collection of liquid waste in a comfortable manner. Further, such a position allows the wearer to wear any type of outer garments 44 that may not otherwise be practical or possible. These factors free the wearer and aid in the participation in activities that may have otherwise been impossible or uncomfortable.

Further, the outlet tube 38, flexible tube 34 and valve 36 provides for a discreet method of expelling such waste liquid 50. The configuration of the outlet tube 38, hose 34 and valve 36 provide for use of standard facilities liquid waste 50 disposal in a substantially normal manner. Further, evacuation of the collection chamber 12 does not require removal of outer garments 44.

Figure 4:
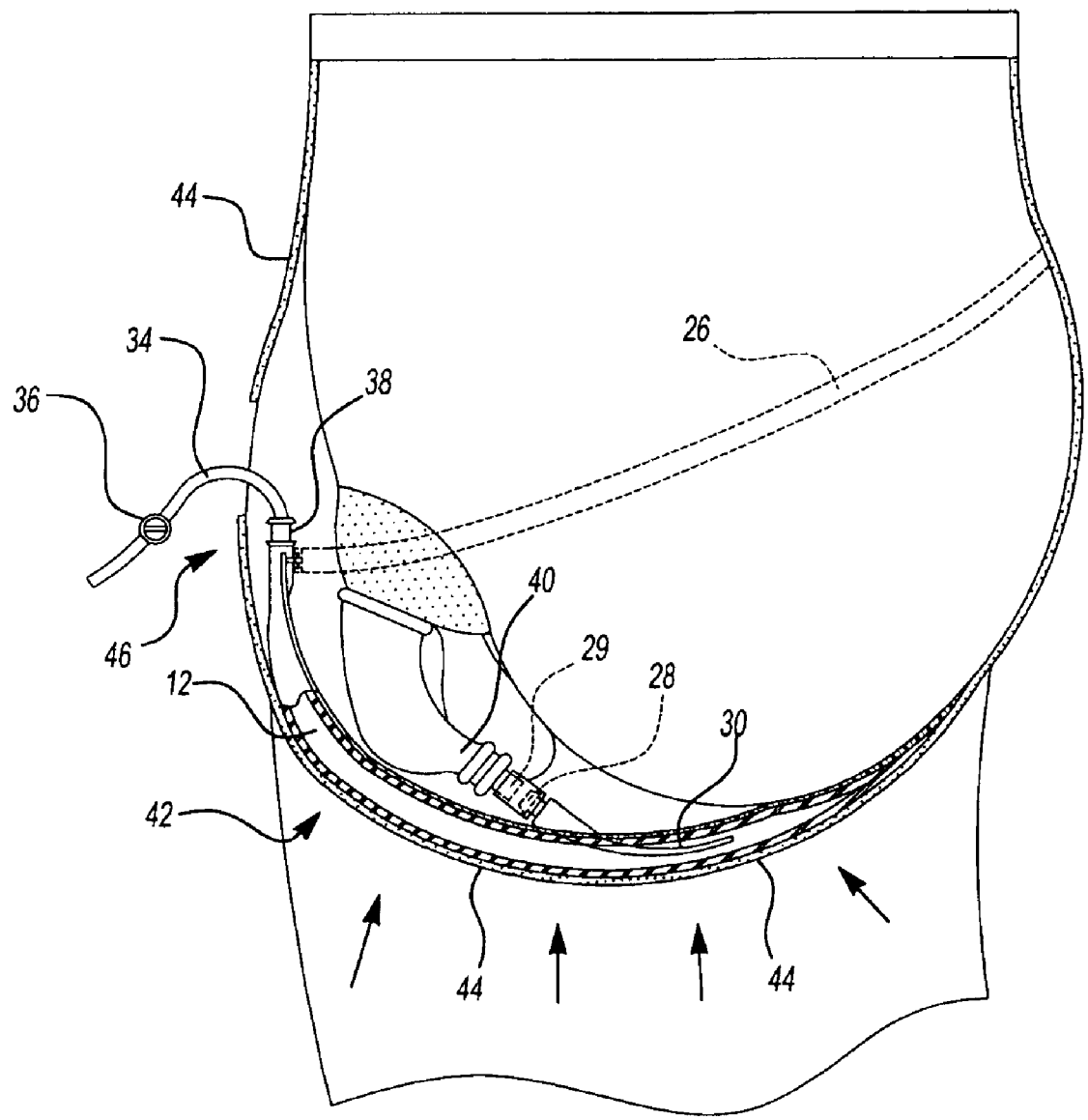
FIG. 4 is a side view of the collection chamber configured for emptying.

Referring to FIG. 4, the assembly 10 of this invention is shown in a discharge state. In this state, the outlet tube 34 is extended from the outergarment 44 through an opening or fly 46. The outlet valve 36 is opened and pressure is applied to the bottom portion of the collection chamber 12 as is indicated by arrows 44. The pressure as indicated by arrows 44 drives the liquid waste 50 from the collection chamber through outlet tube 38, flexible tube 34 and outlet valve 36. The liquid waste is expelled into an ordinary collection receptacle in much the same manner as is used by non-incontinent males. This provides for the discrete disposal and evacuation of liquid waste which further enhances the freedom and comfort to the wearer.

The collection chamber 12 of this invention provides a discrete, comfortable and convenient method of collecting and disposing of liquid waste while allowing the wearer to participate in activities that otherwise may not have been possible due to the restraining and uncomfortable devices required to accommodate the wearer's incontinence.

As appreciated, the straps and button arrangement to secure the collection chamber 12 to the wearer in the crotch region as indicated by 42, is only one way of securing the collection chamber and other such as Velcro strips, specific undergarments designed for holding of the collection chamber and other devices as is known to the art are within the contemplation of this invention. Further, the specific triangular shape of the collection chamber 12 is designed to provide easy wearability of the collection chamber to a wearer and adpation to the crotch region of the wearer.

Further, although the specific examples and embodiments illustrated in the figures, are adapted for use by incontinent males it is within the contemplation of this invention that the collection chamber 12 of this invention may be adapted for the wearing and use of incontinent females by way of using a catheter specifically adapted for use by females.

The foregoing description is exemplary and not just a material specification. The invention has been described in an illustrative manner, and should be understood that the terminology used is intended to be in the nature of words of description rather than of limitation. Many modifications and variations of the present invention are possible in light of the above teachings. The preferred embodiments of this invention have been disclosed, however, one of ordinary skill in the art would recognize that certain modifications are within the scope of this invention. It is understood that within the scope of the appended claims, the invention may be practiced otherwise than as specifically described. For that reason the following claims should be studied to determine the true scope and content of this invention.

What is claimed is:

1. A urine collection assembly worn by a user comprising:
   a collection chamber comprising a flat triangular bag having a top edge, first and second side edges, and a bottom segment, said side edges converging downwardly from opposite ends of said top edge to a point adjacent said bottom segment, said collection chamber adapted for mounting in a crotch region of the user;
   a catheter adapted to collect urine;
   an inlet tube in fluid communication with said catheter at a first end and said collection chamber on a second end, said second end disposed at a point below said catheter, such that urine flows from said catheter through said inlet tube into said collection chamber; and
   an outlet tube disposed above said inlet tube, and in fluid communication with said collection chamber for expelling urine, said outlet tube including a valve movable between open and closed positions.

2. The assembly of claim 1, further including a back flow preventer valve disposed between said tube and said collection chamber for preventing flow of urine out of said chamber through said tube.

3. The assembly of claim 2, wherein said back flow preventer valve is a check valve.

4. The assembly of claim 2, wherein said tube is rigid and attached to said collection chamber and said catheter includes a flexible tube attached to said rigid tube providing fluid communication between said catheter and said collection chamber.

5. The assembly of claim 1, further including the method of expelling urine from said collection chamber including the steps of opening said valve and applying pressure to said collection chamber to expel urine through said outlet tube.

6. The assembly of claim 1, wherein said catheter is a condom catheter.

7. The assembly of claim 1, further including at least one support strap attached to said topside of said collection chamber and adapted to support said collection chamber on the wearer.

8. The assembly of claim 7, further including a second support strap attached to said common point adapted to secure said collection chamber in a groin region of the wearer.

9. The assembly of claim 1, wherein said collection chamber includes an adhesive for attachment to an undergarment.

10. The assembly of claim 1, wherein said collection chamber expands to accommodate accumulation of fluids.

11. The assembly of claim 1, wherein said collection chamber is formed from a plastic and includes pleats to accommodate increasing volumes of urine.

12. The assembly of claim 1, wherein said collection chamber is formed from a rubber material.

13. A urine collection assembly worn by a user comprising:
   a collection chamber adapted to be worn by a user and concealed under outer garments;
   an outlet tube disposed above an inlet tube, said outlet tube including an outlet valve movable between an open and closed position; and
   a catheter worn by the user to direct urine to an inlet tube; said inlet tube in fluid communication with said catheter at a first end and said collection chamber on a second end, said second end disposed at a point below said catheter such that urine flows unaided by the user from said catheter through said tube into said collection chamber.

14. The assembly of claim 13, wherein said collection chamber includes a top side and two opposing sides beginning at ends of said top side and terminating at a common point disposed below said top side.

15. The assembly of claim 13, further including a check valve for preventing the flow of urine out of said collection chamber.

16. A drainage urine collection device adapted to be worn in the crotch region of a user comprising:
   a substantially triangular collection chamber having a top edge and first and second side edges extending from opposing ends of said top edge and converging at a common apex, the chamber comprising a top sheet and a bottom sheet bonded together along said top and side edges;
   a rigid inlet tube attached to the top sheet at a point between said top edge and said apex in fluid communication with an interior of said collection chamber, said inlet tube extending substantially parallel to said top sheet directed towards said top edge for direct coupling to a urine drainage catheter, such that urine flows from said catheter through said inlet tube downwardly into said collection chamber;
   a rigid outlet tube extending from said top edge in a direction opposite to said apex and in fluid communication with said interior of said collection chamber; and
   a securing means attached to the collection chamber and adapted to secure said collection chamber in the crotch region of the user.

17. The urine collection device as recited in claim 16, comprising a back flow preventer valve in fluid communication with said inlet tube and disposed downstream within the interior of said collection chamber.

18. The urine collection device as recited in claim 16, comprising a flexible outlet tube connected to the rigid outlet tube and including an outlet drain valve, to controllably expel collected urine.

19. The urine collection device as recited in claim 16 wherein said inlet tube is attached to the top sheet adjacent said apex.

20. The urine collection device as recited in claim 16, wherein said top and bottom sheets comprise a flexible liquid and gas impermeable material.

21. The assembly as recited in claim 1, wherein said inlet tube comprises an elbow inlet.

22. The assembly as recited in claim 1, wherein said collection chamber comprises a plastic material.

23. The assembly as recited in claim 3, wherein said back flow preventer valve comprises an elbow flap check valve.

* * * * *